United States Patent [19]

Wingen et al.

[11] Patent Number: 5,641,428
[45] Date of Patent: Jun. 24, 1997

[54] USE OF OPTICALLY ACTIVE 1,3-DIOXOLANE-4-CARBOXYLATES AS DOPES IN LIQUID-CRYSTAL MIXTURES, LIQUID-CRYSTAL MIXTURES CONTAINING THESE COMPOUNDS, AND NOVEL OPTICALLY ACTIVE 1,3-DIOXOLANE-4-CARBOXYLATES

[75] Inventors: Rainer Wingen, Hattersheim am Main; Hans-Rolf Dübal, Königstein/Taunus; Claus Escher, Mühltal; Wolfgang Hemmerling, Sulzbach; Ingrid Müller, Hofheim am Taunus; Dieter Ohlendorf, Liederbach, all of Germany

[73] Assignee: Hoechst Aktiengesellschaft, Frankfurt, Germany

[21] Appl. No.: 879,147

[22] Filed: Apr. 30, 1992

Related U.S. Application Data

[63] Continuation of Ser. No. 494,909, Mar. 9, 1990, abandoned, which is a continuation of Ser. No. 181,925, Apr. 15, 1988, abandoned.

[30] Foreign Application Priority Data

Apr. 18, 1987 [DE] Germany ............ 37 13 273.3

[51] Int. Cl.$^6$ ............................................ C09K 19/34
[52] U.S. Cl. ............................................. 252/299.61
[58] Field of Search ................................ 252/299.61

[56] References Cited

U.S. PATENT DOCUMENTS

| | | | |
|---|---|---|---|
| 4,336,183 | 6/1982 | Nakahara et al. | 524/95 |
| 4,873,019 | 10/1989 | Krause et al. | 252/299.61 |

FOREIGN PATENT DOCUMENTS

| | | | |
|---|---|---|---|
| 306195 | 3/1989 | European Pat. Off. | 252/299.61 |
| 3604898 | 8/1987 | Germany. | |
| 3604899 | 8/1987 | Germany. | |
| 3739588 | 7/1988 | Germany. | |

OTHER PUBLICATIONS

Takenaka et al., Mol. Cryst. Liq. Cryst., vol. 131, pp. 257–271 (1985).

CA 74:3148t(1971).

CA 84:163740q (1976).

Morrison and Boyd, Organic Chemistry, 4th Ed., pp. 786–787 (1983).

Chemical Abstracts, vol. 88, p. 566, No. 22089e (Jan. 1978).

Chemical Abstracts, vol. 88, p. 566, No. 22094c (Jan. 1978).

*Primary Examiner*—Cynthia Harris Kelly
*Attorney, Agent, or Firm*—Curtis, Morris & Safford, PC

[57] ABSTRACT

Optically active, mesogenic 1,3-dioxolane-4-carboxylates are suitable as dopes in liquid-crystal mixtures. They result in liquid-crystalline ferroelectric phases having short switching times and in electroclinic phases having large electroclinic coefficients. Their particular advantage is that they induce a helix of very large pitch, meaning that helix compensation by further dopes is unnecessary. In addition, the 1,3-dioxolane-4-carboxylates exhibit high UV stability.

6 Claims, No Drawings

USE OF OPTICALLY ACTIVE 1,3-DIOXOLANE-4-CARBOXYLATES AS DOPES IN LIQUID-CRYSTAL MIXTURES, LIQUID-CRYSTAL MIXTURES CONTAINING THESE COMPOUNDS, AND NOVEL OPTICALLY ACTIVE 1,3-DIOXOLANE-4-CARBOXYLATES

This application is a continuation of application Ser. No. 07/494,909, filed Mar. 9, 1990, now abandoned, which is a continuation of application Ser. No. 07/181,925 filed Apr. 15, 1988, now abandoned.

DESCRIPTION

Especially in the last decade, liquid crystals have been introduced into a very wide variety of industrial areas in which electrooptical and display device properties are in demand (for example in displays for watches, pocket calculators and typewriters). These display devices are based on dielectric alignment effects in nematic, cholesteric and smectic phases of liquid-crystalline compounds, where—caused by the dielectric anisotropy—the longitudinal molecular axis of the compounds adopts a preferred alignment in an applied electric field. The usual switching times in these display devices are rather too slow for many other potential areas of application of liquid crystals, which are per se very promising chemical compounds for industry due to their unique properties. This disadvantage is particularly noticeable when it is necessary to address a large number of image points, which means that the production costs of equipment containing relatively large areas, for example video equipment, oscillographs or TV, radar, ED or word processor screens, would be too high.

Besides nematic and cholesteric liquid crystals, optically active smectic liquid-crystal phases have also become increasingly important in the last few years.

Clark and Lagerwall have been able to show that the use of ferroelectric liquid-crystal systems in very thin cells results in optoelectrical switching or display elements which, compared to conventional TN ("twisted nematic") cells, have switching times which are faster by a factor of up to 1,000 (cf., for example, Lagerwall et al "Ferroelectric Liquid Crystals for Displays", SID Symposium, October Meeting 1985, San Diego, Calif., USA). As a consequence of these and other favorable properties, for example the possibility of bistable switching and the fact that the contrast is virtually independent of the view angle, ferroelectric liquid crystals are in principle highly suitable for the above-mentioned areas of application, for example via matrix addressing.

Another electrooptical effect, known as the electroclinic effect, is exhibited by orthogonal, chiral, smectic phases, for example $S_A^*$, $S_B^*$ and $S_E^*$. This effect (S. Garoff and R. B. Meyer, Phys. Rev. Lett. 38, 848 (1977)) comprises a field-induced tendency of the molecules to alter their tilt angle $\theta$ in proportion with the applied field. The molecules in the orthogonal phase can therefore follow the field change continuously, and they are able, in particular, to follow an alternating field up to a limiting frequency $f_G$, whereas each time ferroelectric systems reach a certain field strength, their tilt angle is changed discretely and retained until a corresponding opposed field is applied (bistable switching).

Both effects, ferroelectric and electroclinic, can be utilized, depending on their specific properties, for the construction of electrooptical switching and display elements. For this purpose, either compounds which form tilted or orthogonal smectic phases and are themselves optically active are required, or chiral, tilted or orthogonal, smectic phases can be induced by doping compounds which, although forming such smectic phases, are not themselves optically active, with optically active compounds. The desired phase here should be stable over the greatest possible temperature range.

In order to achieve a good contrast ratio in electrooptical elements, a uniform planar orientation of liquid crystals is necessary. Good orientation in $S_A^*$ and $S_C^*$ phases can be achieved if the phase sequence for the liquid-crystal mixture as the temperature decreases is:

Isotropic N* $S_A^*$ $S_C^*$.

The prerequisite is that the pitch of the helix in the N* phase is very large (greater than 10 μm) or, even better, is completely compensated for. (T. Matsumoto et al., pp. 468–470, Proc. of the 6th Int. Display Research Conf., Japan Display, Sept. 30–Oct. 2, 1986, Tokyo, Japan; M. Murakami et al., ibid. p. 344–p.347). This is achieved by adding to the chiral liquid-crystal mixture, which has, for example, an anticlockwise helix in the N* phase, a further optically active dope which induces a clockwise helix, in amounts such that the helix is just compensated for.

It has now been found that optically active and mesogenic 1,3-dioxolane-4-carboxylates as dopes in tilted, smectic liquid-crystal phases result in short switching times and, in orthogonal smectic liquid-crystal phases, in high electroclinic coefficients, even when admixed in small amounts. It is particularly surprising here that the pitch of the helix induced by the doping is sufficiently great to render compensation by further dopes unnecessary.

The invention therefore relates to the use of optically active and mesogenic 1,3-dioxolane-4-carboxylates as dopes in liquid-crystal systems. The invention furthermore relates to liquid-crystal systems which contain these 1,3-dioxolane-4-carboxylates, and to novel optically active 1,3-dioxolane-4-carboxylates. The 1,3-dioxolane-4-carboxylates to be used in accordance with the invention as dopes in liquid-crystal mixtures correspond to the general formula (I)

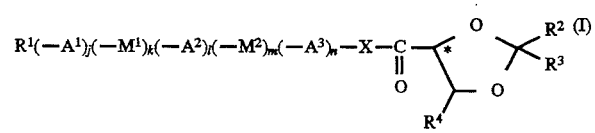

in which the symbols have the following meaning:

$R^1$

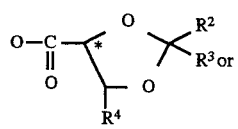

a straight-chain or branched alkyl radical having 1 to 16 carbon atoms or a straight-chain or branched alkenyl radical having 3 to 16 carbon atoms, it being possible for these radicals themselves to contain asymmetrical carbon atoms and it being possible for one or more non-adjacent —$CH_2$— groups to be replaced by —O—, —S—, $$-\underset{\underset{O}{\|}}{C}-,\ -O-\underset{\underset{O}{\|}}{C}-$$

and/or $$-\underset{\underset{O}{\|}}{C}-O-$$

and for one or more H to be replaced by F, Cl, Br or CN,

R² and R³ are each H or an alkyl radical having 1 to 10 carbon atoms, it being possible for one or more H to be replaced by F, or R² and R³, together with the C(2) atom of the dioxolane ring, form a cyclopentane, cyclohexane or cycloheptane ring, R⁴ denotes H or an alkyl radical having 1 to 10 carbon atoms or an alkenyl radical having 2 to 10 carbon atoms, j and l denote zero, 1 or 2, k and m denote zero or 1, n denotes zero, 1 or 2, with the following proviso: if j and/or l are zero, k is zero; if n is zero, m is zero; the sum J+l+n is at least 1 and at most 3, —A¹ and —A² denote

[ring structures: phenyl, cyclohexyl, pyridyl (various N positions), pyrimidyl, pyrazinyl, pyridazinyl, triazinyl, thiadiazolyl, dioxanyl, dithianyl, thiophenyl/furanyl, piperazinyl]

—A³ denotes

[ring structures: phenyl, cyclohexyl, pyridyl, pyrimidyl, pyridazinyl]

—M¹ and —M² denote $$-\underset{\underset{O}{\|}}{C}-O-,\ -O-\underset{\underset{O}{\|}}{C}-,$$

—CH₂CH₂—, —CH=CH—, —CH₂O—, —OCH₂—, and

X denotes O or S.

In a preferred embodiment, the symbols in the general formula (I) have the following meaning:

R¹ denotes a straight-chain or branched alkyl or alkenyl radical which has 4 to 14 carbon atoms and which may contain an asymmetrical carbon atom, or where one —CH₂— group may be replaced by $$-O-,\ -\underset{\underset{O}{\|}}{C}-\ \text{or}\ -\underset{\underset{O}{\|}}{C}-O-,$$

or where one or more H may be replaced by F,

R², R³ and R⁴ denote H or an alkyl radical having 1 to 5 carbon atoms, or R² and R³, together with the C(2) atom or the dioxolane ring, denote a cyclopentane or cyclohexane ring, j and l denote zero or 1, k, m and n denote zero or 1, —M¹ and —M² denote $$-\underset{\underset{O}{\|}}{C}-O-\ \text{or}\ -O-\underset{\underset{O}{\|}}{C}-,$$

and

X denotes O or S.

In a further preferred embodiment, 1,3-dioxolane-4-carboxylates of the general formula (IV)

$$R^5(-M^3)_k-A^4-X-\underset{\underset{O}{\|}}{C}-\overset{*}{\underset{\underset{O}{\diagdown}}{\diagup}}\underset{O}{\overset{CH_3}{\diagdown}}\quad\quad (IV)$$

are employed in which:

R⁵ denotes a straight-chain or branched alkyl or alkenyl radical which has 6 to 12 carbon atoms and which may contain an asymmetrical carbon atom, —M denotes $$-O,\ -S,\ -O-\underset{\underset{O}{\|}}{C}\ \text{or}\ -\underset{\underset{O}{\|}}{C},$$

—A⁴ denotes

[ring structures: biphenyl, pyridyl-phenyl variants]

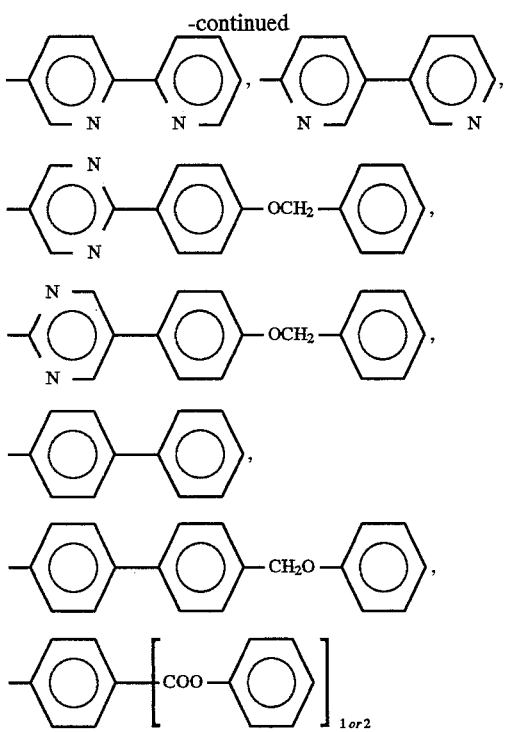

The novel compounds of the general formula (I), in particular (IV), preferably include the compounds mentioned by name in the examples. For the preparation of compounds of the general formula (I), mesogenic phenols or thiophenols of the general formula (II)

$$R^1(-A^1)_j(-M^1)_k(-A^2)_l(-M^2)_m(-A^3)_n-X-H \quad (II)$$

are reacted with suitable derivatives of 1,3-dioxolane-4-carboxylic acid (III), preferably the acyl chlorides (where Y=Cl)

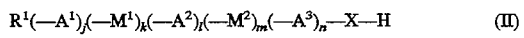

in the presence of equivalent or excess amounts of organic or inorganic bases, if appropriate with the aid of acylating catalysts, in a suitable solvent, and the reaction product is isolated and purified by suitable measures, for example by crystallization, filtration or chromatographic separation methods. Y in this formula is a suitable leaving group, such as Cl, Br, ONa or comparable groups. The phenols to be used are known from the literature. Methods for the preparation of 1,3-dioxolane-4-carboxylic acid derivatives which are suitable in the above sense are likewise known from the literature, for example M. Angrick et al., Monatsheft für Chemie 116, 377 (1985); R. Dumont et al., Helv. Chim. Acta 66, 814 (1983), T. Sugiyama et al., Agric. Biol. Chem. 48, 1841 (1984) or J. Jurczak et al., Tetrahedron 42, 447 (1986). The two components (II) and (III) can be linked to form (I) by methods which are known per se from the literature, such as described, for example, by J.-M. Beau et al., Tetrahedron Letters 26, 6193 (1985).

The liquid-crystal mixtures according to the invention form liquid-crystal phases and contain at least one optically active compound of the general formula (I).

The term "liquid-crystal phase" is taken to mean nematic, cholesteric, orthogonally smectic or tilted smectic phases, in particular $S^*_A$, $S^*_B$ and $S^*_C$ phases. The liquid-crystal mixtures comprise 2 to 20, preferably 2 to 15, components, including at least one of the chiral compounds claimed according to the invention.

The other components are preferably selected from known compounds having nematic, cholesteric and/or smectic phases, for example $S_A$ phases, and/or tilted smectic phases; these include, for example, Schiff bases, biphenyls, terphenyls, phenylcyclohexanes, cyclohexylbiphenyls, N-, S- or O-containing heterocyclic compounds, for example pyrimidines, cinnamates, cholesterol esters and various bridged, multinuclear p-alkylbenzoates with polar terminal groups. In general, the commercially available liquid-crystal mixtures are already present, before addition of the optically active compound(s), as mixtures of a very wide variety of components, of which at least one is mesogenic, i.e. as the compound, in derivatized form or mixed with certain cocomponents, exhibits a liquid-crystal phase which gives expectations of at least one enantiotropic (clear point>melting point) or monotropic (clear point<melting point) mesophase formation. In addition to at least one of the optically active compounds claimed according to the invention, the liquid-crystal mixture contains, in particular, one ester compound having an $S_c$ phase, for example a phenyl alkoxybenzoate, or a biaromatic compound having a nitrogen-containing heterocyclic ring, for example an alkylpyrimidinylalkoxybenzene.

The liquid-crystal mixtures generally contain 0.05 to 70% by weight, in particular 0.1 to 50% by weight, of the compound(s) according to the invention. The compounds according to the invention are suitable, in particular, as dopes for tilted, smectic liquid-crystal phases since they convert the latter into ferroelectric liquid-crystal phases; the values for spontaneous polarization (Ps) at 25° C. are in the range about 8–14 nC/cm$^2$ at doping levels of 10 mol-% and in the range about 80–140 nC/cm$^2$ linearly extrapolated to the pure compound. The switching times for the novel systems are mostly significantly below 50 μs at doping levels of 10 mol-%, 25° C. and a switching voltage of ±10 V/μm.

The compounds according to the invention can also be employed in order to achieve the electroclinic effect in orthogonal, smectic phases ($S^*_A$, $S^*_B$ and $S^*_E$).

EXAMPLE 1

(R)-4-(2-n-octylpyrimidin-5-yl)phenyl 2,2-dimethyl-1,3-dioxolane-4-carboxylate

[(I) where $R^1=C_8H_{17}$, j=1, $-A^1=$

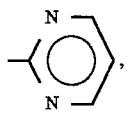

k=l=m=zero, n=1, $-A^3=$

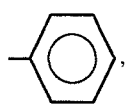

X=O, $R^2=R^3=CH_3$ and $R^4=H$].

1.86 g (11.3 mmol) of 2,2-dimethyl-1,3-dioxolane-4-carbonyl chloride are added over the course of 10 minutes to a solution of 3.2 g (11.3 mmol) of 4-(2-n-octylpyrimidin-5-yl)phenol, 1.24 g (12.3 mmol) of triethylamine and 10 mg of 4-dimethylaminopyridine in 30 ml of tetrahydrofuran at 0° C. After the mixture has been stirred for three hours at 0° C, the triethylammonium hydrochloride is filtered off and the filtrate is dried in vacuo.

After chromatographic purification and recrystallization from n-hexane, 1.6 g (34.3% of theory) of colorless crystals of melting point 88° C are obtained;

$[\alpha]_D^{21}$: +7.54 (c=5, CDCl$_3$). The following are obtained analogously

EXAMPLE 2

(R)-4-(2-n-octyloxypyrimidin-5-yl)phenyl 2,2-dimethyl-1,3-dioxolane-4-carboxylate

[(I) where $R^1=H_{17}C_8O$, j=1, —A$^1$=

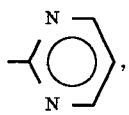

k=l=m=zero, n=1, —A$^3$=

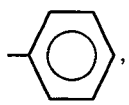

X=O, $R^2=R^3=CH_3$, and $R^4$=H]
Melting point 85° C. $[\alpha]_D^{20}$: +7.1 (c=1.1, CDCl$_3$)

Example 3

(R)-4-(2-n-octylthiopyrimidin-5-yl)phenyl 2,2-dimethyl-1,3-dioxolane-4-carboxylate

[(I) where $R^1=H_{17}C_8S$, j=1, —A$^1$=

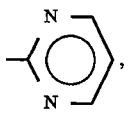

k=l=m=zero, n=1, —A$^3$=

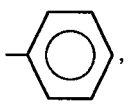

X=O, $R^2=R^3=CH_3$, $R^4$=H]
Melting point 75° C. $[\alpha]_D^{20}$: +7.8 (c=1.1, CDCl$_3$).

EXAMPLE 4

(R)-4-(5-n-octylpyrimidin-2-yl)phenyl 2,2-dimethyl-1,3-dioxolane-4-carboxylate

[(I) where $R^1=H_{17}C_8$, j=1, —A$^1$=

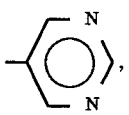

k=l=m=zero, n=1, —A$^3$=

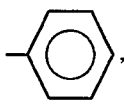

X=O, $R^2=R^3=CH_3$, $R^4$=H]
Melting point 87° C. $[\alpha]_D^{20}$: 9.0 (c=5, CDCl$_3$)

EXAMPLE 5

(R)-4-(5-n-octyloxypyrimidin-2-yl)phenyl 2,2-dimethyl-1,3-dioxolane-4-carboxylate

[(I) where $R^1=H_{17}C_8O$, j=1, —A$^1$=

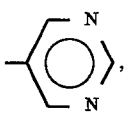

k=l=m=zero, n=1, —A$^3$=

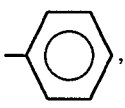

X=O, $R^2=R^3=CH_3$, $R^4$=H]
Melting point 112° C. $[\alpha]_D^{20}$: +11.0 (c=5, CDCl$_3$)

EXAMPLE 6

(R)-(4'-octyloxybiphenyl-4-yl) 2,2-dimethyl-1,3-dioxolane-4-carboxylate

[(I) where $R^1=H_{17}C_8O$, j=k=l=m=zero, n=2, —A$^3$=

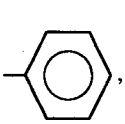

X=O, $R^2=R^3=CH_3$ and $R^4$=H]
Melting point 115° C. $[\alpha]_D^{20}$: +7.9 (c=1, CDCl$_3$)

EXAMPLE 7

(R),(R)-4,4'-dihydroxydiphenyl bis(2,2-dimethyl-1,3-dioxolane-4-carboxylate)

[(I) where $R^1$=2,2-dimethyl-1,3-dioxolane-4-carbonyloxy-, j=k=l=m=zero, n=2, —A$^3$=

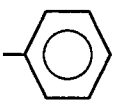

X=O, $R^2=R^3=C_3$ and $R^4$=H]
Melting point 196° C. $[\alpha]_D^{20}$: +14.7 (c=5, CDCl$_3$)

EXAMPLE 8

(R)-[4-(4-decyloxybenzoyloxy)phenyl]2,2-dimethyl-
1,3-dioxolane-4-carboxylate

[(I) where $R^1=H_{21}C_{10}O$, j=1, —$A^1$=

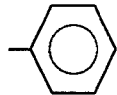

k=l=zero, m=1, —$M^2$=

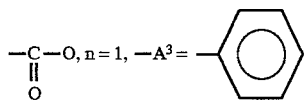

X=O, $R^2=R^3=CH_3$ and $R^4=H$]
Melting point 94° C. $[\alpha]_D^{20}$: +5.5 (c=2.2 $CDCl_3$)

EXAMPLE 9

(R)-4-(2-n-octylthiopyrimidin-5-yl)phenyl 2,2-
pentamethylene-1,3-dioxolane-4-carboxylate

[(I) where $R^1=H_{17}C_8S$, j=1, —$A^1$=

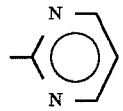

k=l=m=zero, n=1, —$A^3$=

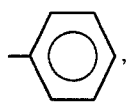

X=O, $R^2+R^3=(CH_2)_5$, $R^4=H$]
Melting point 90.8° C. $[\alpha]_D^{20}$: +15.1 (c=5, $CH_2Cl_2$)

EXAMPLE 10

(R)-4-(2-n-octyloxypyrimidin-5-yl)phenyl 2,2-
pentamethylene-1,3-dioxolane-4-carboxylate

[(I) where $R^1=H_{17}C_8O$, j=1, —$A^1$=

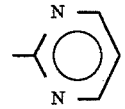

k=l=m=zero, n=1, —$A^3$=

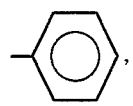

X=O, $R^2+R^3=(CH_2)_5$ and $R^4=H$]
Melting point 90.1° C. $[\alpha]_D^{20}$: +13.6 (c=5, $CH_2Cl_2$)

EXAMPLE 11

(R)-4-(5-n-hexylpyrimidin-2-yl)phenyl 2,2-
dimethyl-1,3-dioxolane-4-carboxylate

[(I) where $R^1=H_{13}C_6$, j=1, —$A^1$=

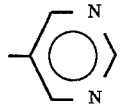

k=l=m=zero, n=1, —$A^3$=

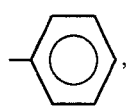

X=O, $R^2=R^3=CH_3$ and $R^4=H$]
Melting point 88.5° C. $[\alpha]_D^{20}$: +11.0 (c=7, $CHCl_3$)

EXAMPLE 12

(R)-4-[2-((S)-7-methylnonyloxy)pyrimidin-5-yl]
phenyl 2,2-dimethyl-1,3-dioxolane-4-carboxylate

[(I) where $r^1=H_5C_2CH(CH_3)(CH_2)_6O$, j=1, —$A^1$=

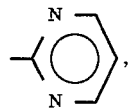

k=l=m=zero, n=1, —$A^3$=

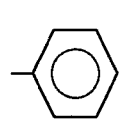

X=O, $R^2=R^3=CH_3$ and $R^4=H$]
Melting point 76° C. $[\alpha]_D^{20}$: +10.2 (c=5, $CH_2Cl_2$)

EXAMPLE 13

(R)-4-(5-n-octylpyrimidin-2-yl)phenyl 2,2-
pentamethylene-1,3-dioxolane-4-carboxylate

[(I) where $R^1=H_{17}C_8$, j=1, —$A^1$=

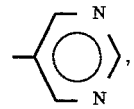

k=l=m=zero, n=1, —$A^3$=

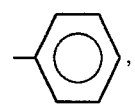

X=O, $R^2+R^3=(CH_2)_5$ and $R^4=H$]
Melting point 96.8° C. $[\alpha]_D^{20}$: +16.6 (c=5, $CH_2Cl_2$)

EXAMPLE 14

(R)-4-(2-n-octylpyrimidin-5-yl)phenyl 2,2-pentamethylene-1,3-dioxolane-4-carboxylate

[(I) where $R^1=H_{17}C_8$, j=1, —$A^1$=

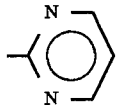

k=l=m=zero, n=1, —$A^3$=

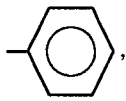

X=O, $R^2+R^3=(CH_2)_5$ and $R^4$=H]
Melting point 85.4° C. $[\alpha]_D^{20}$: +15.0 (c=5, $CH_2Cl_2$)

EXAMPLE 15

(R)-4-(5-n-nonylpyrimidin-2-yl)phenyl 2,2-dimethyl-1,3-dioxolane-4-carboxylate

[(I) where $R^1=H_{19}C_9$, j=1, —$A^1$=

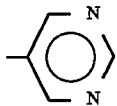

k=l=m=zero, n=1, —$A^3$=

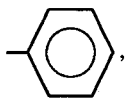

X=O, $R^2=R^3=CH_3$ and $R^4$=H]
Melting point 92.4° C. $[\alpha]_D^{20}$: +8.8 (c=7.5, $CHCl_3$)

EXAMPLE 16

(R)-4-(5-n-decylpyrimidin-2-yl)phenyl 2,2-dimethyl-1,3-dioxolane-4-carboxylate

[(I) where $R^1=H_{21}C_{10}$, j=1, —$A^1$=

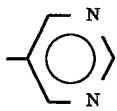

k=l=m=zero, n=1, —$A^3$=

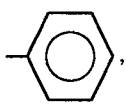

X=O, $R^2=R^3=CH_3$ and $R^4$=H]
Melting point 88° C. $[\alpha]_D^{20}$: +9.2 (c=5, $CHCl_3$)

EXAMPLE 17

(R)-4-(5-n-undecylpyrimidin-2-yl)phenyl 2,2-dimethyl-1,3-dioxolane-4-carboxylate

[(I) where $R^1=H_{23}C_{11}$, j=1, —$A^1$=

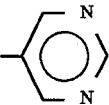

k=l=m=zero, n=1, —$A^3$=

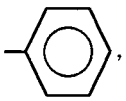

X=O, $R^2=R^3=CH_3$ and $R^4$=H]
Melting point 89.7° C. $[\alpha]_D^{20}$: +9.6 (c=5, $CHCl_3$)

EXAMPLE 18

(R)-4-[2-(4-hexylphenyl)pyrimidin-5-yl]phenyl 2,2-dimethyl-1,3-dioxolane-4-carboxylate (I) where $R^1=H_{13}C_6$, j=l=n=1, k=m=zero, —$A^1$=—$A^3$=

—$A^2$=

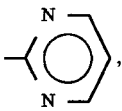

$R^2=R^3=CH_3$ and $R^4$=H]
Phase sequence C 159° $S_3$ 173° $S_C$ 190° $S_A$ 196° I $[\alpha]_D^{20}$:+8.7 (C=2. $CHCl_3$)

EXAMPLE 19

(R)-4-[5-(4-hexylphenyl)pyrimidin-2-yl]phenyl 2,2-dimethyl-1,3-dioxolane-4-carboxylate

[(I) where $R^1=H_{13}C_6$, j=l=n=1, k=m=zero, —$A^1$=—$A^3$=

—$A^2$=

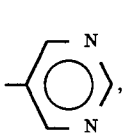

X=O, $R^2=R^3=CH_3$ and $R^4$=H]
Phase sequence 157° $S_3$ 162° $S_C$ 178° $S_A$ 195° I $[\alpha]_D^{20}$: +10.1 (c=2, $CHCl_3$)

EXAMPLE 20

(R)-[2-(4-dodecyloxyphenyl)]pyrimidin-5-yl 2,2-dimethyl-1,3-dioxolane-4-carboxylate

[(I) where $R^1=H_{25}C_{12}O$, j=1, —$A^1$=

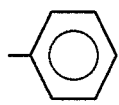

l=l=m=zero, —$A^3$=

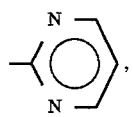

X=O, $R^2=R^3=CH_3$ and $R^4$=H]
Melting point 97° C. $[\alpha]_D^{20}$: +6.9 (c=2 CHCl$_3$)

EXAMPLE 21

(R)-[2-<4-(5-oxohexyl)oxyphenyl>]pyrimidin-5-yl 2,2-dimethyl-1,3-dioxolane-4-carboxylate

[(I) where $R^1=H_3C(C=O)(CH_2)_4O$, j=1, —$A^1$=

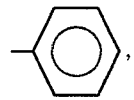

k=l=m=zero, n=1, —$A^3$=

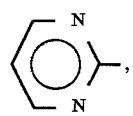

X=O, $R^2=R^3=CH_3$ and $R^4$=H]
Melting point 139° C. $[\alpha]_D^{20}$: +7.9 (c=2, CHCl$_3$)

EXAMPLE 22

(R)-[2-<4-(4-trans-pentylcyclohexyl)carbonyloxyphenyl>]-pyrimidin-5-yl 2,2-dimethyl-1,3-dioxolane-4-carboxylate

[(I) where $R^1=H_{11}C_5$, j=k=l=n=1, m=zero, —$A^1$=

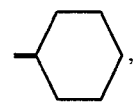

—$M^1$=

—$A^2$=

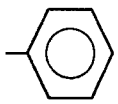

—$A^3$=

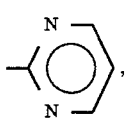

X=O, $R^2=R^3=CH_3$ and $R^4$=H]
Phase sequence C 154° N* 204° I
$[\alpha]_D^{20}$: +6.6 (c=2, CHCl$_3$)

EXAMPLE 23

(R)-[2-(4-pentylcarbonyloxyphenyl)]pyrimidin-5-yl 2,2-dimethyl-1,3-dioxolane-4-carboxylate

[(I) where $R^1$=

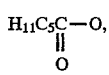

j=1, —$A^1$=

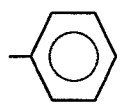

k=l=m=zero, n=1, —$A^3$=

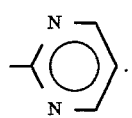

X=O, $R^2=R^3=CH_3$ and $R^4$=H]
Melting point 115.5° C. $[\alpha]_D^{20}$: +8.4 (c=2, CHCl$_3$)

EXAMPLE 24

(R)-[4-<2-(4-decyloxyphenyl)methyleneoxypyrimidin-5-yl>]phenyl 2,2-dimethyl-1,3-dioxolane-4-carboxylate

[(I) where $R^1=H_{21}C_{10}O$, j=k=l=n=1, m=zero, —$A^1$=

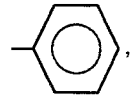

—$M^1$=—$CH_2O$, —$A^2$=

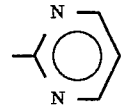

—A³=

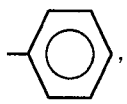

X=O, R²=R³=CH₃ and R⁴=H]

Phase sequence C 107° S_A 125° I $[\alpha]_D^{20}$: +5.7 (c=2, CH₂Cl₂)

EXAMPLE 25

(R)-[2-(5-octylpyrid-2-yl)]phenyl 2,2-dimethyl-1,3-dioxolane-4-carboxylate

[(I) where R¹=H₁₇C₈, j=1, —A¹=

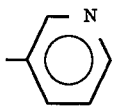

k=l=m=zero, n=1, —A³=

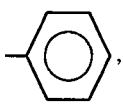

X=O, R²=R³=CH₃ and R⁴=H]

Melting point 107° C. $[\alpha]_D^{20}$: +10.1 (c=2, CHCl₃)

EXAMPLE 26

(R)-4-[2-(4-hexyloxyphenyl)pyrimidin-5-yl)phenyl 2,2-dimethyl-1,3-dioxolane-4-carboxylate

[(I) where R¹=H₁₃C₆O, j=l=n=1, k=m=zero,

—A¹= 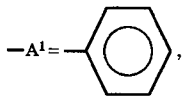

—A²= 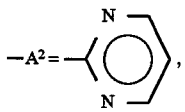

—A³= 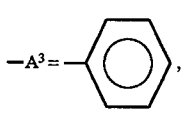

X=O, R²=R³=CH₃ and R⁴=H]

Clear point 209° C. $[\alpha]_D^{20}$: +7.9 (c=2, CHCl₃)

EXAMPLE 27

(R)-[4-(4-trans-propylcyclohexyl)]phenyl 2,2-dimethyl-1,3-dioxolane-4-carboxylate

[(I) where R¹=H₇C₃, j=1, —A¹=

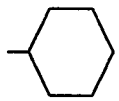

k=l=m=zero, n=1, —A³=

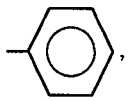

X=O, R²=R₃=CH₃ and R⁴=H]

Melting point 99.1° C. $[\alpha]_D^{20}$: +7.1 (c=2, CHCl₃)

EXAMPLE 28

(R)-[4'-(4-octyloxybenzoyloxy)]biphenyl-4-yl 2,2-dimethyl-1,3-dioxolane-4-carboxylate

[(I) where R¹=H₁₇C₈O, j=k=l=1, —A³=

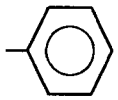

—M¹=—C—O, l=m=zero, n=2, —A³=

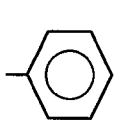

X=O, R²=R³=CH₃ and R⁴=H]

Phase sequence C 146.5° S_A 165.5° N* 200.5° I
$[\alpha]_D^{20}$: +5.75 (c=2, CHCl₃)

EXAMPLE 29

(R)-[4-<2-(1,1-H-perfluorooctyl)oxypyrimidin-5-yl>]phenyl 2,2-dimethyl-1,3-dioxolane-4-carboxylate

[(I) where R¹=F₁₅C₇CH₂O, j=1, —A¹=

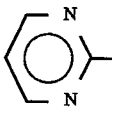

k=l=m=zero, n=1, —A³=

X=O, R²=R³=CH₃ and R⁴=H]
Phase sequence C 107° S_A 125° I
$[\alpha]_D^{20}$: +3.9 (c=2, CH₂Cl₂)

EXAMPLE 30

(R)-4-[5-(4-hexyloxyphenyl)pyrimidin-2-yl]phenyl 2,2-dimethyl-1,3-dioxolane-4-carboxylate

[(I) where $R^1=C_{13}H_6O$, j=l=n=1, k=m=zero,

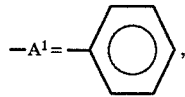

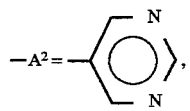

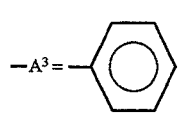

X=O, $R^2=R^3=CH_3$ and $R^4$=H]
Clear point 213° C. $[\alpha]_D^{20}$: +5.9 (c=2, CHCl$_3$)

EXAMPLE 31

(R)-[4-(5-octyl-1,3-dioxan-2-yl)phenyl]2,2-dimethyl-1,3-dioxolane-4-carboxylate

[(I) where $R^1=H_{17}C_8$, j=1, —A$^1$=

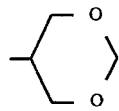

k=l=m=zero, n=1, —A$^3$=

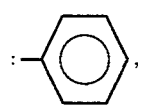

X=O, $R^2=R^3=CH_3$ and $R^4$=H]
Melting point C 104.3° C. I $[\alpha]_D^{20}$: +5.9 (c=2, CHCl$_3$)

EXAMPLE 32

(R)-[4-(5-octyl-1,3-dithian-2-yl)phenyl]2,2-dimethyl-1,3-dioxolane-4-carboxylate

[(I) where $R^1$ $H_{19}C_8$, j1, —A$^1$=

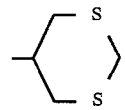

k=l=m=zero, n=1, —A$^3$=

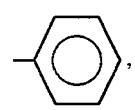

X=O, $R^2=R^3=CH_3$ and $R^4$=H]
Melting point C 129.1° C. I $[\alpha]_D^{20}$: +7.1 (c=2, CHCl$_3$)

EXAMPLE 33

(R)-4-(5-n-octyloxypyrimidin-2-yl)phenyl 2,2-pentamethylene-1,3-dioxolane-4-carboxylate

[(I) where $R^1=H_{17}C_8$, j=1, —A$^1$=

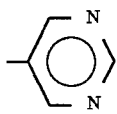

X=O, $R^2+R^3=(CH_2)_5$ and $R^4$=H, k=l=m=zero, n=1, —A$^3$=

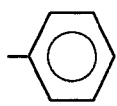

Melting point C 111.4° I $[\alpha]_D^{20}$: +15.5 (c=2, CH$_2$Cl$_2$)

EXAMPLE 34

(R)-[2-(4-octyloxyphenyl)]pyrimidin-5-yl 2,2-pentamethylene-1,3-dioxolane-4-carboxylate

[(I) where $R^1=H_{17}C_8O$, j=1, —A$^1$=

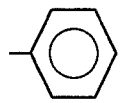

k=l=m=zero, n=1, —A$^3$=

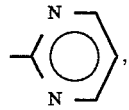

X=O, $R^2+R^3=(CH_2)_5$ and $R^4$=H]
Melting point C 111.6° I $[\alpha]_D^{20}$: +16.1 (c=2, CHCl$_3$)
Measurement method:

If a small amount of a chiral compound is added to a (non-chiral) solvent, the plane of linear-polarized light is rotated through the (characteristic) angle α; this angle is specified as follows: $[\alpha]_D^T$ (c=x, S), where the symbols have the following meanings: x=concentration of the solution in g/l, S=solvent, D=589 nm (Na D line), T=temperature of the solution. The angle of rotation is determined in a polarimeter after a light path length of 10 cm.

Use Examples A1 to A18

In order to test the effectiveness of the above-described compounds as ferroelectric dopes in liquid-crystal systems having tilted smectic phases, these compounds are mixed, in concentrations of 10 mol-% in each case, with the racemate of the compound

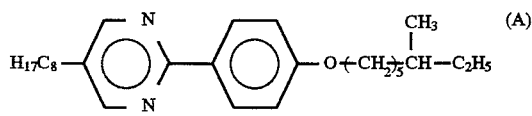

(A)

Phase sequence: C 14.9° C. $S_c$ 49.8° C. $S_A$ 59.2° C. I (5° C.)

4-(5-octylpyrimidin-2-yl)-1-(6-methyloct-1-oxy) benzene, or of the compound

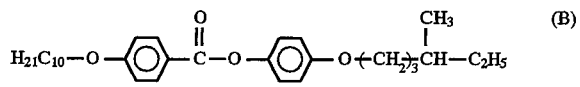

Phase sequence: C 17° C. $S_G$ 32.7° C. $S_c$ 70.4° C. $S_A$ 73.3° C. (–3° C.)

4-(4-decyloxyphenyl-1-carbonyloxy)-1-(4-methylhexyloxy)benzene, or of a non-chiral test mixture (C) having the phase sequence: C 13.2° C. $S_c$ 51° C. $S_A$ 61.2° C. N 66.7° C. I, or of a non-chiral test mixture (D) having the phase sequence C 12.5° C. $S_c$ 83° C. $S_A$ 95° C. N 100° C. I, and the values for spontaneous polarization ($P_s$ in nC.cm$^{-2}$), for the switching time τ (in μs) and for the optical tilt angle of the $S_c$ phase θ (in °) of the mixture are determined in each case. The $P_s$ values are measured by the method of H. Diamant et al. (Rev. Sci. Instr., 28, 30, 1957), where a special-purpose measuring cell [Skarp et al. in Ferroelectric Letters Vol. 06, 67 (1986)] is used in which the τ and μ values are also determined. At a cell path length of about 2 μm, a uniform planar orientation of the liquid crystals in the $S_c$ phase is achieved by shearing [SSFLC technique, Clark et al., Appl. Phys. Lett. 36, 899 (1980)]. In order to determine τ and θ, the measuring cell is clamped to the rotating stage of a polarizing microscope between crossed analyzer and polarizer. The optical tilt angle or switching angle 2θ is determined by rotating the measuring cell from maximum to minimum light transmission. The switching time τ is determined with the aid of a photodiode by measuring the time taken for the light signal to increase from a signal level of 10 to 90%. The switching voltage is ±10 V/μm. In addition to the values for $P_s$, τ, and 2θ, the $S_c$ range of the respective mixture is given, where the values in parentheses indicate the supercoolable lower temperature limit for the $S_c$ region. When compounds (A), (B), (C) and (D) are used as host for accommodation of the dope, all the values for $P_s$, τ and 2θ relate to a temperature of 25° C. (40° C.).

TABLE 1

| (Substance) example | Use example | Host | $s_c$* region of the mixture in °C. | $P_s$ nC/cm$^2$ | τ μs | 2 θ |
|---|---|---|---|---|---|---|
| 1 | A1 | A | 31[4] – 54 | 14 | 55 | 52 |
| 2 | A2 | A | 37[0] – 53 | 12.5 | 35 | 50 |
| 3 | A3 | A | 29,5[4] – 51 | 11.5 | 50 | 49 |
| 4 | A4 | A | 13[1] – 51 | 9 | 25 | 41 |
| 5 | A5 | A | 18[6] – 52 | 8 | 40 | 41 |
| 6 | A6 | A | [14] – 57 | 8.3 | 45 | 46 |
| 8 | A7 | B | 35[35] – 69 | 9.5 | 50 | 59 |
| 11 | A8 | C | 15[–8] – 43 | 9.8 | 33 | 40 |
| 13 | A9 | C | 11[–5] – 50 | 12.0 | 30 | 46 |
| 15 | A10 | C | 12[–7] – 47 | 8.6 | 25 | 40 |
| 16 | A11 | C | 15[–6] – 51 | 8.8 | 18 | 41 |
| 17 | A12 | C | 17[–6] – 50 | 7.9 | 25 | 37 |
| 10 | A13 | D | 10[–6] – 78 | 26.2 | 37 | 64 |
| 12 | A14 | D | 11[–10] – 75 | 23.0 | 35 | 64 |
| 20 | A15 | D | [20] – 82 | 18.1 | 52 | 63 |
| 22 | A16 | D | | 18* | 12* | 64* |
| 25 | A17 | D | [5] – 82 | 20.2 | 76 | 61 |
| 33 | A18 | D | [10] – 80 | 22.3 | 33 | 63 |

*at 60° C.

Use examples A19 and A20

A non-chiral liquid-crystal mixture having the phase sequence I→N→$S_A$→$S_C$ was admixed with each of the compounds according to the invention, and the twisting capability (induction of helix) in the nematic phase was investigated. The pitch of the induced helix was determined, as described, for example, by P. Kassubek et al., Mol. Cryst. Liq. Cryst., Vol. 8, pages 305 to 314, 1969, in a wedge cell having an orientation layer by measuring the displacement lines under the polarizing microscope. Table 2 collates the results. As can be seen from the table, both examples exhibit such a large pitch in the N* phase, even at a doping level of 10 mol-%, that pitch compensation by a further optically active dope is not necessary. Example A20 even exhibits helix inversion, which means that the helix changes its direction of rotation and the pitch of the helix becomes infinite.

TABLE 2

| (Substance) example | Use example | Proportion of the compound in mol-% | Temperature °C. | Pitch μm | Direction of rotation of the helix*) | HTP**) 1/μm |
|---|---|---|---|---|---|---|
| 4 | A19 | 10 | 60 | 30 | – | –0.33 |
| 6 | A20 | 8 | 65 | 49.3 | – | –0.25 |
| 6 | A20 | 8 | 63.5 | ∞ | | |
| 6 | A20 | 8 | 62.4 | 46.6 | + | +0.27 |

– (anticlockwise)
+ (clockwise)
**)HTP (helical twisting power) = (X · p)$^{-1}$
X = molar fraction of the dope
p = pitch Use examples A21 and A22

In orthogonal smectic phases ($S_A$, $S_B$ and $S_E$), the compounds of the formula (I) induce the electroclinic effect, the magnitude of which is given by the differential coefficient (dθ/dE). θ is the tilt angle induced by the electrical field E. This parameter is measured in the $S_A$* phase, but in the same "bookshelf" arrangement and in the same cell as used for the polarization measurements (see Use examples A1 to A18). The tilt angle induced by the electrical field is measured in the polarizing microscope with crossed polarizers by locating the dark positions, reading off the pertinent angle on the rotating stage and subtracting from this the angle measured without an applied field. In order to test the effectiveness of the compounds (I), the electroclinic coefficient of two mixtures was determined. The first (Example A21) was a mixture of (substance) Example 2 (X=0.1) in the racemate A (X=0.9). The second (Example A22) was (substance) Example 4 (X=0.1) with which a non-chiral base mixture of phase sequence I→N→$S_A$→$S_c$→C was doped. The values determined in the $S_A$* phases thus obtained are collated in Table 3. (X=molar fraction).

TABLE 3

| | Electroclinic coefficients | |
|---|---|---|
| Use example | t [°C.] | (dθ/dE) [10$^{-9}$ rad m/V] |
| A21 | 56 | 2.2 |
| A22 | 49 | 5.9 |
| A22 | 51 | 3.3 |
| A22 | 53 | 2.0 |

We claim:
1. An optically active 1,3-dioxolane-4-carboxylate of the formula (I)

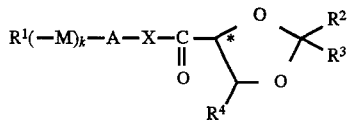 (I)

in which:

R¹ is

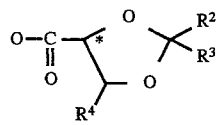

or a straight-chain or branched alkyl radical having 1 to 16 carbon atoms or a straight-chain or branched alkenyl radical having 3 to 16 carbon atoms, it being possible for these radicals to contain asymmetrical carbon atoms and it being possible for one or more nonadjacent —CH₂— groups to be replaced by —O—, —S—,

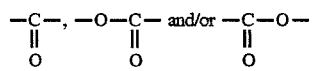

and for one or more H to be replaced by F, Cl, Br or CN, R² and R³ are each H or an alkyl radical having 1 to 10 carbon atoms, it being possible for one or more H of the alkyl radicals to be replaced by F; or R² and R³, together with the C(2) atom of the dioxolane ring, form a cyclopentane, cyclohexane or cycloheptane ring, R⁴ is H or an alkyl radical having 1 to 10 carbon atoms or an alkenyl radical having 2 to 10 carbon atoms, k is zero or 1, with the following proviso that k is zero, if R¹ is a dioxolane group or an alkyl group with a replaced —CH₂— group, —A— is:

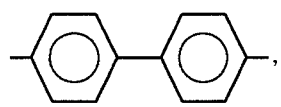

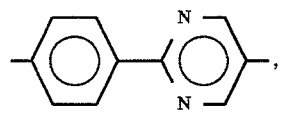

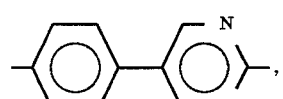

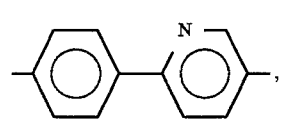

-continued

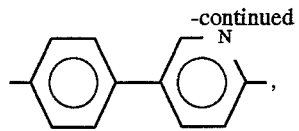

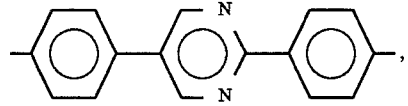

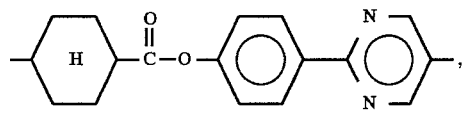

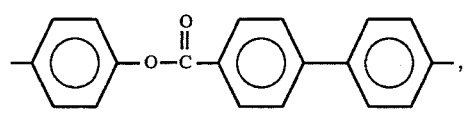

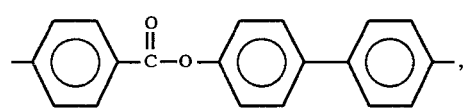

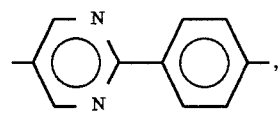

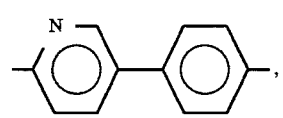

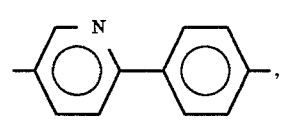

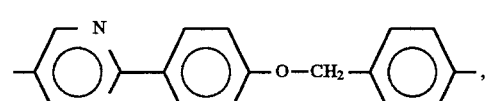

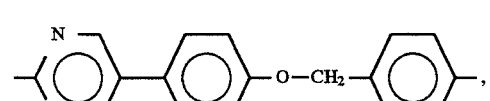

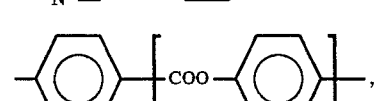

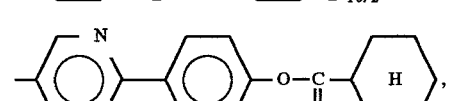

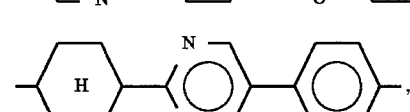

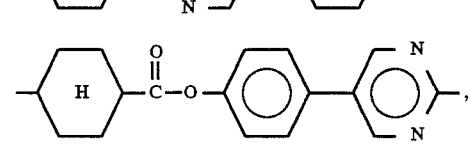

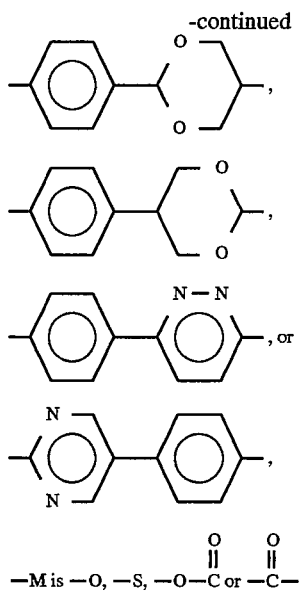

—M is —O, —S, —O—C(=O)— or —(O=)C—O— and

—X is —O or —S.

2. An optically active 1,3-dioxolane-4-carboxylate of the formula (I) of claim 1, in which $R^1$ is a straight-chain or branched alkyl or alkenyl radical which has 6 to 12 carbon atoms and which may contain asymmetrical carbon atoms, —M is —O, —S,

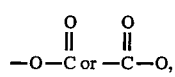

$R^2$ and $R^3$ are $CH_3$ or $R^2$ and $R^3$ together with the C(2) atom of the dioxolane ring form —$(CH_2)_5$—, $R^4$ is H, —X is —O or —S, k is zero or 1, and —A— is:

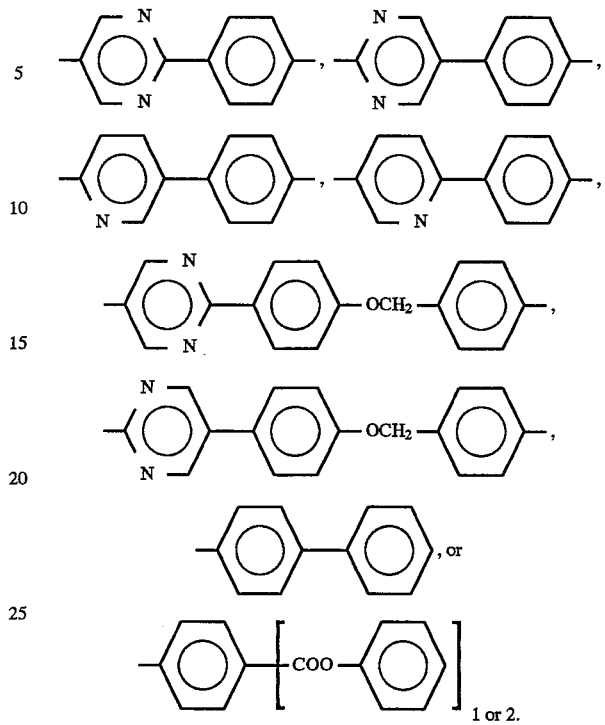

3. A liquid-crystal mixture containing at least one optically active compound of the formula (I) of claim 1 and a component selected from compounds having nematic, cholesteric and/or smectic phases.

4. A liquid-crystal mixture containing at least one optically active compound of the formula (I) of claim 2 and a component selected from compounds having nematic, cholesteric and/or smectic phases.

5. An electrooptical switching or display element containing a liquid-crystal mixture as claimed in claim 3.

6. An electrooptical switching or display element containing a liquid-crystal mixture as claimed in claim 4.

* * * * *